United States Patent
Charness et al.

(10) Patent No.: US 6,359,015 B1
(45) Date of Patent: Mar. 19, 2002

(54) METHOD FOR ANTAGONIZING INHIBITION EFFECTS OF ALCOHOL ON CELL ADHESION

(75) Inventors: Michael E. Charness, Waban; Michael F. Wilkemeyer, Allston, both of MA (US)

(73) Assignee: The United States of America as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 09/793,533

(22) Filed: Feb. 27, 2001

Related U.S. Application Data
(60) Provisional application No. 60/185,264, filed on Feb. 28, 2000.

(51) Int. Cl.[7] .............................................. A61K 31/045
(52) U.S. Cl. ....................................................... 514/724
(58) Field of Search ......................................... 514/724

(56) References Cited

U.S. PATENT DOCUMENTS

| | | |
|---|---|---|
| 5,496,851 A | 3/1996 | Grinnell |
| 6,169,071 B1 | 1/2001 | Blaschuk |
| 6,169,072 B1 | 1/2001 | Jonczyk et al. |

OTHER PUBLICATIONS

Charness, M.E., Simon, R.P. & Greenberg, D.A., Ethanol and the Nervous System, *N. Engl. J. Med.*, Aug. 17, 1989, vol. 321, pp. 442–454.
Diamond, I & Gordon, A.S., Cellular and Molecular Neuroscience of Alcoholism, *Physiological Reviews*, Jan. 1997, vol. 77, pp. 1–20.
Harris, R.A., Ethanol Actions on Multiple Ion Channels; Which are Important? *Alcohol Clin Exp.* Res, 1999. vol. 23, pp 1563–1570.
Peoples, R. W., Li, C. & Weight, F. F., Lipid vs Protein Theories of Alcohol Action in the Nervous System, *Ann. Rev. Pharmacol. Toxicol.* 1996, vol. 36, pp. 185–201.
Franks, N.P. & Lieb, W. R., Molecular Mechanism of General Anaesthesia, Nature, Dec. 9, 1982, vol. 300, pp. 487–493.
Wick, M. J., Mihic, S. J., Ueno, S., Mascia, M. P., Trudell, J. R., Brozowski, S. J., Ye, Q., Harrison, N. L. & Harris R. A., Mutations of γ–Aminobutyric Acid and Glycine Receptors Change Alcohol Cutoff: Evidence for An Alcohol Receptor, *Proc. Natl. Acad. Sci.*, May 1998, vol. 95, pp. 6504–6509.
Dwyer, D. S. & Bradley, R. J., Chemical Properties of Alcohols and Their Protein Binding Sites, *Cell Mol. Life Sci.* 2000, vol. 57, pp. 265–275.
Charness, M. E., Safran, R. M & Perides, G., Ethanol Inhibits Neural Cell–Cell Adhesion, *J. Biol. Chem.*, Mar. 25, 1994, vol. 269, pp. 9304–9309.

Ramanathan, R., Wilkemeyer, M. F., Mittal, B., Perides, G. & Charness, M. E., Alcohol Inhibits Cell–Cell Adhesion Mediated by Human L1, *J. Cell Biol.* Apr. 1996, vol. 133, pp. 381–390.
Wilkemeyer, M. F. & Charness, M. E., Characterization of Ethanol–Sensitive and Insensitive Fibroblast Cell Lines Expressing Human L1, *J. Neurochem.* 1998, vol. 71, pp. 2382–2391.
Wilkemeyer, M. F., Pajerski, M. & Charness, M. E., Alcohol Inhibition of Cell Adhesion in BMP–Treated NG108–15 Cells, *Alcohol Clin. Exp. Res.* Nov. 1999, vol. 23, pp. 1711–1720.
Bearer. C. F., Swick, A. R., O'Riordan, M. A. & Chang, G., Ethanol Inhibits L1–Mediated Neurite Outgrowth in Postnatal Rat Cerebellar Granule Cells, *J. Biol. Chem.* May 7, 1999, vol. 274, No. 19, pp. 13264–13270.
McCreery, M. J & Hunt, W.A., Physico–Chemical Correlates of Alcohol Intoxication, Neuropharmacol. 1978, vol. 17, pp. 451–461.
Charness, M. E, Querimit, L. A. & Diamond, I., Ethanol Increases the Expression of Functional Delta–Opioid Receptors in Neuroblastoma x Glioma NG108–15 Hybrid Cells, *J. Biol. Chem.*, Mar. 5, 1986, vol. 261, No. 7, pp. 3164–3169.
Perides, G., Safran, R. M. Rueger, D. C. & Charness, M. E., Induction of the Neural Cell Adhesion Molecule and Neuronal Aggregation by Osteogenic Protein 1, *Proc. Natl. Acad. Sci.*, Nov. 1992, vol. 89, pp. 10326–10330.
Perides, G., Hu, G., Rueger, D. C. & Charness, M. E., Osteogenic Protein–1 Regulates L1 and Neural Cell Adhesion Molecule Gene Expression in Neural Cells, *J. Biol. Chem.* Nov. 25, 1993, vol. 268, No. 33, pp. 25197–25205.
Perides, G., Safran, R. M., Downing, L. A. & Charness, M. E., Regulation of Neural Cell Adhesion Molecule and L1 by the Transforming Growth Factor–β Superfamily, *J. Biol. Chem.* Jan. 7, 1994, vol. 269, No. 1, pp. 765–770.
Lewohl, J. M., Wilson, W. R., Mayfield, R.D., Brozowski, S. J., Morrisett, R. A. G–Protein–Coupled inwardly rectifying Potassium Channels are Targets of Alcohol Action, *Nat. Neurosci*, Dec. 1999, vol. 2, No. 12, pp. 1084–1090.
Vallejo, Y., Hortsch, M. & Dubreuil, R. R., Ethanol Does Not Inhibit the Adhesive Activity of Drosphila Neuroglian or Human L1in Drosphilia S2 Tissue Culture Cells, *J. Biol. Chem.*, May 2, 1997, vol. 272, No. 18, pp. 12244–12247.
Wong, E. V., Kenwrick, S., Willems, P. & Lemmon, V., Mutations in the Cell Adhesion Molecule L1 Cause Metal Retardation, *Trends Neurosci.* 1995, vol. 18, No. 4, pp. 168–172.
Luthi, A., Laurent, J. P., Figurov, A., Muller, D. & Schachner, M. Hippocampal Long–Term Potentiation and Neural Cell Adhesion Molecules L1 and NCAM, *Nature*, Dec. 1994, vol. 372, pp. 777–779.

*Primary Examiner*—William R. A. Jarvis
(74) *Attorney, Agent, or Firm*—Dinesh Agarwal, P.C.

(57) ABSTRACT

A method of antagonizing inhibition effects of alcohol on cell adhesion, includes contacting a cell-adhesion molecule expressing cell with an effective amount of a compound, wherein the compound comprises an alcohol with five or more carbons. More particularly, the compound comprises 1-pentanol, 1-octanol, and structural derivatives thereof.

9 Claims, 7 Drawing Sheets

| Alcohols | 1-Butanol | 3-Methyl-1-Butanol | 2-Ethyl-1-Butanol | 3,3-Dimethyl-1-Butanol |
|---|---|---|---|---|
| Structure |  |  |  |  |
| IC50 (uM) | 350 | 290 | 230 | 50 |
| Pm/b | 1.5 | 2.9 | 9.1 | 5.8 |
| Vm | 92 | 109 | 123 | 121 |

METHOD FOR ANTAGONIZING INHIBITION EFFECTS OF ALCOHOL ON CELL ADHESION

This application claims priority based on prior U.S. Provisional Application, Ser. No. 60/185,264, filed Feb. 28, 2000, and which is incorporated herewith in its entirety by reference.

FIELD AND HISTORICAL BACKGROUND OF THE INVENTION

The present invention is directed to inhibiting alcohol effects on cell adhesion, and more particularly to method and compound for antagonizing inhibition effects of alcohol on cell adhesion, and further to the use of alcohol inhibition antagonists in prophylaxis or treatment of toxic effects of alcohol.

Alcoholism is a major public health problem in the United States, costing the nation approximately $167 billion annually as a result of medical expenses, accidents, alcohol-related violence, and lost productivity. Two common neurological disorders associated with drinking are fetal alcohol syndrome (FAS) and memory disorders. FAS is a common and preventable cause of mental retardation that results from heavy maternal drinking during pregnancy. FAS affects about one in 1,000 U.S. infants and about 6 percent of the offspring of alcoholic mothers. Children with FAS exhibit mental retardation, growth retardation, malformations of the brain, face, and heart, and behavioral disorders, while children with less severe fetal alcohol effects exhibit neurobehavioral deficits. In addition, alcohol abuse can lead to neurological disorders in adults, disrupting memory and learning.

The brain malformations result in part from a failure of neurons (nerve cells) to migrate correctly from their place of origin to their destination during brain development. Neuronal migration depends heavily on the actions of cell adhesion molecules, which are chemical tags that protrude from nerve cell membranes and stick to like molecules on adjacent cells or other molecules in the extracellular space. Cell adhesion molecules guide neuronal migration during the formation of the nervous system, and their disruption results in brain malformations.

L1 is a cell adhesion molecule that plays a critical role in brain development. Children with mutations in the gene for L1 have brain malformations similar to those seen in children with FAS. Previously, we found that ethanol inhibits the adhesiveness of some cells that have been engineered to express human L1, suggesting that ethanol's effects on this molecule might contribute to FAS. L1 may also play an important role in learning and memory in the mature nervous system. The finding was striking because of the similarity in brain lesions between children with mutations in the gene for L1 and children with fetal alcohol syndrome. Cell adhesion molecules, such as L1, influence neuronal migration and the extension and bundling of neuronal processes, functions that are essential for normal human nervous system development. L1 is also believed to play a role in long-term synaptic changes that may influence learning and memory.

Ethanol is known to cause serious injury to both the developing and mature nervous system (Reference 1). Recent evidence suggests that alcohols alter nervous system function by interacting directly with selective neural proteins, including ion channels, kinases, and transporters (References 2 and 3). Experiments with the homologous series of 1-alcohols reveal different cutoffs for alcohol effects on diverse native and purified proteins (References 4–6). For alcohols below the cutoff, potency increases as a function of increasing hydrophobicity; alcohols above the cutoff are less potent or inactive. The inactivity of 1-alcohols of greater hydrophobicity, than those below the cutoff, has been taken as evidence that the active 1-alcohols interact with protein rather than lipid sites. The size of the alcohol cutoff for the $GABA_A$ (a receptor for the neurotransmitter GABA) and glycine receptors can be manipulated by substituting single amino acids within the transmembrane region of a protein subunit (Reference 7), indicating a striking degree of target specificity. Diverse alcohol targets appear to comprise a hydrophobic crevice that binds methyl groups and a hydrophilic allosteric site that interacts with the hydroxyl group (Reference 8).

L1 is an immunoglobulin cell adhesion molecule that regulates neuronal migration, axon fasciculation (bundling of nerve processes), and growth cone guidance (leading edge of actively extending nerve processes), through homophilic and heterophilic interactions (Reference 9). We have shown that clinically-relevant concentrations of ethanol inhibit cell-cell adhesion mediated by L1 in transfected fibroblasts and in the NG108-15 neuroblastoma×glioma cell line (derived from rat and mouse tumors) (References 10–13). In NG108-15 cells, ethanol also inhibits morphogenetic changes induced by BMP-7 (growth factor that induces expression of L1 in neural cells), a powerful inducer of L1 and N-CAM (cell adhesion molecule different from L1) gene expression (Reference 10). Because of the similarity in brain lesions in children with fetal alcohol syndrome and those with mutations in the gene for L1, we have speculated that ethanol effects on L1 could play a role in the pathophysiology of fetal alcohol syndrome (Reference 11). Interestingly, ethanol potently inhibits L1-mediated neurite extension in cerebellar granule cells (Reference 14).

1-alcohol inhibition of cell-cell adhesion demonstrates an abrupt cutoff effect between 1-butanol and 1-pentanol (References 10–11), consistent with a direct effect on L1 or an associated protein.

U.S. Pat. Nos. 5,496,851; 6,169,071; and 6,169,072, are directed to method and compounds for modulating or inhibiting cell-cell adhesion.

Although increasing evidence suggests that alcohols act within specific binding pockets of selective neural proteins, however, antagonists at these sites have not yet been identified.

OBJECTS AND SUMMARY OF THE INVENTION

The present invention is based on the discovery that 1-alcohols from methanol through 1-butanol inhibit with increasing potency the cell-cell adhesion mediated by the immunoglobulin cell adhesion molecule L1. The inventors surprisingly found that an abrupt cutoff exists after 1-butanol, with 1-pentanol and higher 1-alcohols showing no effect, and that strict structural requirements must be met for alcohol inhibition of cell-cell adhesion in L1-transfected NIH/3T3 (a rat fibroblast cell line) and in NG108-15 neuroblastoma×glioma hybrid cells treated with BMP-7, an inducer of L1 and N-CAM. The target site discriminates the tertiary structure of straight-chain and branched-chain alcohols and appears to comprise both a hydrophobic binding site and an adjacent hydrophilic allosteric site. Modifications to the 2- and 3-carbon positions of 1-butanol increased potency, whereas modifications that restrict movement about the 4-carbon abolished activity. The effects of ethanol and 1-butanol on cell-cell adhesion were antagonized by 1-pentanol ($1C_{50}$=715 $\mu$M) and 1-octanol ($IC_{50}$=3.6 $\mu$M). Antagonism by 1-octanol was complete, reversible, and non-competitive. 1-octanol also antagonized ethanol inhibition of BMP-7 morphogensis in NG108-15 cells. 1-Octanol and related compounds are believed to prove useful in determining the role of altered cell adhesion in ethanol-induced injury of the nervous system.

The principal object of the present invention is to provide a method and compound for antagonizing inhibition effects of alcohol on cell adhesion. This is based on the discovery that straight-chain and branched-chain alcohols have highly specific structural requirements for inhibition of cell-cell adhesion. We discovered that 1-pentanol and 1-octanol completely abolish the effects of ethanol and 1-butanol on cell-cell adhesion, and that the effects of ethanol are on the morphogenetic actions of BMP-7.

Another object of the present invention is to provide a method and compound for the prophylaxis or treatment of neurotoxic effects of alcohol, particularly beverage alcohol, i.e., ethanol.

An additional object of the present invention is to provide a method and compound for the prophylaxis or treatment of fetal alcohol syndrome, memory disorders, malformations of the brain, cognitive learning disorders, neuro behavioral disorders, neurological disorders, teratogenesis, and alcohol-related memory disorder and alcohol addiction in adults.

In accordance with the present invention, a method of antagonizing inhibition effects of alcohol on cell adhesion, includes contacting a cell-adhesion molecule expressing cell with an effective amount of a compound, wherein the compound comprises an alcohol with five or more carbons. More particularly, the compound comprises 1-pentanol, 1-octanol, and structural derivatives thereof.

BRIEF DESCRIPTION OF THE DRAWINGS

The above and other objects, novel features and advantages of the present invention will become apparent from the following detailed description of the invention, as illustrated in the drawings, in which.

DETAILED DESCRIPTION OF THE INVENTION

Figure 1:
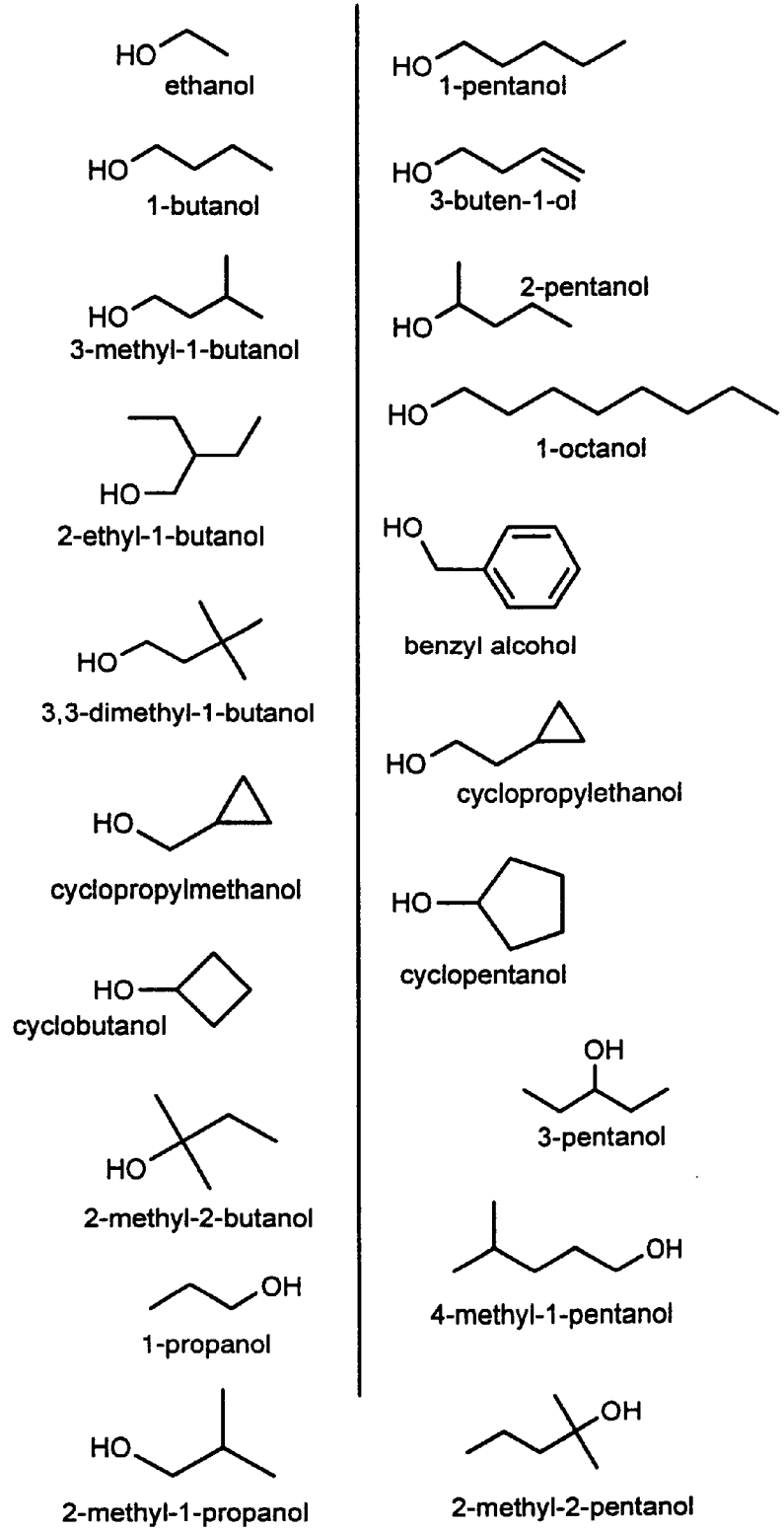
FIG. 1 illustrates structural activity relationship of various alcohols categorized as Active (inhibit cell adhesion) or Inactive (do not inhibit cell adhesion)

The present invention is based on the discovery that long-chain alcohols antagonize the effects of short-chain alcohols on cell adhesion. In particular, we discovered that ethanol and other alcohols interact in a highly specific manner with cells that express the L1 cell adhesion molecule.

Straight-chain alcohols with one to four carbons (methanol, ethanol, propanol, and butanol) show increasing potency in inhibiting cell adhesion, whereas straight-chain alcohols with five or more carbons are inactive. This suggests that small alcohols bind within a protein pocket of limited size to inhibit cell adhesion. The activity of butanol, a four-carbon alcohol, can be abolished by restricting movement between the third and fourth carbon. In contrast, adding carbon groups to the second and third carbon of butanol creates a series of molecules with greater potency than butanol. These findings suggest that ethanol and other small alcohols fit within a well-defined binding pocket of a target protein to inhibit cell adhesion in the same manner as drugs like morphine and Valium interact with very specific regions of their receptors.

The existence of a specific binding pocket for ethanol predicts the discovery of drugs that can block its effects. Strikingly, very low concentrations of both the five-carbon alcohol, pentanol, and the eight-carbon alcohol, octanol, abolish the effects of ethanol on cell adhesion. Octanol also blocks the effects of ethanol on the shape and growth pattern of cultured neural cells. Cultured neural cells that express L1 tend to grow in adherent clusters that form two- and three-dimensional structures. Ethanol inhibits the formation of these clusters, and octanol blocks this action of ethanol. We believe that octanol would be useful in identifying actions of ethanol on the brain that result from the inhibition of cell adhesion.

Our findings, we believe, would lead to the development of drugs that could prevent the damaging effects of ethanol in the nervous system. Although octanol by itself may be too toxic to be used a drug for alcoholics, drugs containing suitable, pharmaceutically acceptable concentration and amounts of octanol, or drugs related to the structure of octanol, are likely to be less toxic and equally effective.

EXAMPLE 1

This example illustrates inhibition of cell-cell adhesion by various alcohols and a non-volatile anesthetic.

Reagents

Alcohols were obtained from Sigma-Aldrich (Sigma Chemical Company, St. Louis, Mo.). All other chemicals were obtained from Sigma, or as indicated. The values for membrane/buffer partition coefficients ($P_{m/b}$) of the alcohols were derived from a published source (Reference 15) or calculated by dividing the octanol/water partition coefficient by 5.

Cell Culture

NIH/3T3 cells were cultured in Dulbecco's minimum Eagle medium (DMEM) (Life Technologies, Gaithersburg, Md.) supplemented with 10% normal calf serum (Intergen, Purchase, N.Y.) and 400 $\mu$g/ml G418 (Life Technologies). NG108-15 neuroblastoma×glioma cells (passages 21 to 30) were plated in serum-free, defined medium (Reference 16). At the start of the morphogenetic and cell adhesion assays, serum-free medium containing BMP-7 (Creative BioMolecules, Hopkinton, Ma.) (1–40 ng/ml, final) was added daily to the NG108-15 cells. Both cell lines were cultured at 37° C., in an atmosphere of 90% air and 10% $CO_2$. Three NIH/3T3 subclones were utilized in these studies: 2B2-L1, 2A2-L1 and Vec-1A5. The 2B2-L1 and 2A2-L1 cell lines are subclones derived from a stable transfection of NIH/3T3 cells with the human L1 cDNA, and Vec-1A5 is a subclone from a transfection with the empty expression vector (Reference 12).

Morphogenetic Actions of BMP-7 in NG108 Cells

NG108-15 cells were plated from suspensions of single cells at a density of 50,000 cells/well in poly-D-lysine-coated, 6-well plated containing serum-free medium in the absence or presence of BMP-7, as described (References 17–18). Following the addition of ethanol (50 mM, final) the plates were sealed with parafilm to prevent evaporation. Control cultures were treated similarly. The media for all cells was replaced daily following the addition of ethanol. At 1–3 days after the addition of ethanol, two randomly-selected, subconfluent (<50%) fields of cells were viewed at 100–200×magnification and evaluated for he presence of cell clusters. A cell cluster was defined as a group of three or more cells that adhered to each other along at least one quarter of their cell bodies (Reference 19). The percentage of cells in clusters was calculated by dividing the number of cells present in clusters by the total number of cells (150 to 200) in each field. Values obtained for each field of a treatment group were then averaged.

Cell Adhesion Assay

Cells were cultured and cell adhesion assays were performed in the absence and presence of the alcohols listed below in Table 1. The concentrations of alcohols used in the adhesion assays were calculated to produce membrane concentrations equivalent to 50–100 mM ethanol. Membrane/buffer partition coefficients ($P_{m/b}$) were obtained or were calculated from published octanol/water partition coefficients (Reference 15). Molar volumes were obtained from published sources (References 15) or were calculated from molecular weights and densities at 20° C. The alcohols are listed in Table 1 by increasing membrane/buffer partition coefficients (with the exception of the non-volatile anesthetic propofol).

Cell-cell adhesion was measured using a modified short-term aggregation assay of sub-confluent cells (Reference 12). Cells were detached by gentle agitation, mechanically dissociated to obtain a single-cell suspension, and diluted in PBS supplemented with 0.1 mg/ml DNase to 350,000 cells/ml for the NIH/3T3 cells, and 250,000 cells/ml for the NG108-15 cells. One ml of the cell suspension was added per well (4.5 cm$^2$) of a 12-well plate. After addition of the alcohols, the cells were gently mixed and mechanically shaken for 30 minutes at room temperature on an orbital shaker set at 60 to 80 rpm. Cells were viewed at a final magnification of 200×, and each well was scored for single and adherent cells in five or six microscopic fields of view. We counted approximately 100 cells per field of view and 600 cells per well. The percentage of adherent cells was calculated for each microscopic field of view and averaged. To calculate the magnitude of ethanol inhibition, we subtracted the values for cell adhesion with the Vec-1A5 cells from those of the 2B2-L1 or 2A2-L1 cell lines. Similarly, the values for cell adhesion in NG108-15 cells cultured in serum-free medium were subtracted from those of NG108-15 cells treated with BMP-7.

EXAMPLE 2

This example illustrates the effects of 1-alcohols on cell-cell adhesion in two model systems.

We tested the effects of a series of alcohols on cell-cell adhesion in two well-characterized model systems. NG108-15 cells were incubated for 48 hours in a serum-free medium supplemented with 10–20 ng/ml BMP-7 to induce L1 and N-CAM gene expression (Reference 10). Parallel experiments were performed using two ethanol-sensitive NIH/3T3 cell lines transfected with human L1 (2B2-L1 and 2A2-L1) (Reference 12) and a NIH/3T3 cell line transfected with the empty expression vector (1A5-V). FIG. 1 depicts the structures of the alcohols used in this invention and categorizes them as Active (inhibits cell-cell adhesion) or Inactive (no effect on cell-cell adhesion). For each alcohol tested, similar results were obtained in BMP-7 treated NG108-15 cells and in L1-expressing NIH/3T3 cells (see Table 1 below).

Treatment with BMP-7 greatly increased the percentage of adherent NG108-15 cells (control, 17.0±1.1%; BMP-7, 50.0±1.4%). Similarly, L1 transfected NIH/3T3 cells exhibited higher levels of cell-cell adhesion than vector-transfected cells (1A5-V, 19.4±1.1%; 2B2-L1, 46.1±1.0%; 2A2-L1, 55.9±2.1%). Consistent with earlier reports (References 10 and 12), 100 mM ethanol or 2 mM 1-butanol maximally inhibited cell adhesion in both cellular systems. In contrast, cell-cell adhesion was not inhibited by concentrations of 1-pentanol (5 mM) and 1-octanol (0.15 mM) that disorder cell membranes to the same extent as 200–300 mM ethanol (Reference 15). We also observed a cutoff for cyclic alcohols; cyclobutanol inhibited cell-cell adhesion, whereas cyclopentanol and benzyl alcohol did not. The inactivity of several alcohols (1-pentanol, 1-octanol, cyclopropyl ethanol, 4-methyl-1-pentanol, 3-buten-1-ol, and cyclopentanol) was confirmed using concentrations 5–10 fold higher than those reported in Table 1. An anesthetic concentration of the non-volatile anesthetic propofol did not inhibit cell-cell adhesion. Therefore, we do not believe that alcohol or anesthetic effects on cell-cell adhesion play a role in intoxication.

EXAMPLE 3

The following is an example of structure activity analysis of the alcohol target site.

We first examined alcohols related to 1-butanol, the 1-alcohol that most potently inhibited cell-cell adhesion. 2-Pentanol differs from 1-butanol through the addition of a methyl group at the 1-carbon position. This slight modification abolished activity (Table 1). In contrast, the addition of up to two methyl groups at the 2-carbon and 3-carbon positions of 1-butanol (2-ethyl-1-butanol; 3-methyl-1-butanol; and 3,3-dimethyl-1-butanol) did not reduce activity. Thus, we do not believe that alcohol activity is a simple function of molecular volume or the total number of carbons.

Modifications to the 4-carbon position of 1-butanol were also informative. 1-cyclopropylethanol differs from 1-butanol through the addition of a methyl group that bonds to both the 3-carbon and 4-carbon atoms to form a cyclopropyl moiety (FIG. 1). This modification abolished activity. To determine whether the inactivity of 1-cyclopropylethanol is related to its bulky cyclopropyl group, we examined several additional cyclic alcohols. Cyclopropylmethanol, a cyclic derivative of 1-propanol, was active, as were the related alcohols, 1-propanol and 2-methyl-1 propanol (Table 1). Another effect of the cyclopropyl modification in 1-cyclopropylethanol is to constrain rotation about the 4-carbon position of 1-butanol. To investigate whether rotation about this axis is necessary for activity, we tested 3-buten-1-ol, a molecule that differs from 1-butanol only in the presence of a double bond between the 3- and 4-carbons. This small modification abolished activity. Thus, the target site appeared to discriminate among the structurally related alcohols.

EXAMPLE 4

The following is an example of an analysis of alcohols as multivalent ligands.

If alcohol action has strict structural requirements, then it is likely that potent alcohols, such as 1-butanol, must align with the target site in a specific orientation to inhibit cell-cell adhesion. Alcohols that present multiple 1-butanol moieties have a higher probability of aligning correctly with a 1-butanol recognition site and should, therefore, be more potent than 1-butanol.

Figure 2:
FIG. 2 illustrates the relationship between the number of 1-butanol moieties and the potency for alcohol inhibition of cell adhesion.
Figure 2:
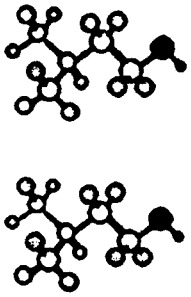
Figure 2:
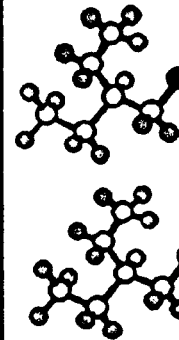
Figure 2:
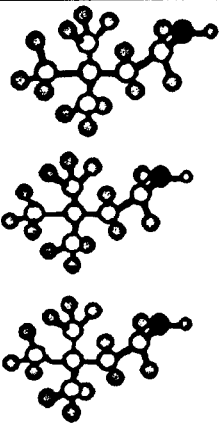

FIG. 2 shows the structure of several multivalent alcohols related to 1-butanol. Dose response curves for the mean percent inhibition of cell adhesion in BMP-7 treated NG108-15 cells were calculated from 3–6 independent experiments. The $IC_{50}$ was determined by log-logit analysis of the mean data. The number of alignments that can present a 1-butanol moiety to a target are depicted for each alcohol. Also illustrated in FIG. 2 is the membrane/buffer partition coefficient ($P_{m/b}$) and molar volume (Vm) of each alcohol. It is noted that 3,3-dimethyl-1-butanol, which can present a 1-butanol moiety from three possible alignments, is less lipid soluble than 2-ethyl-1-butanol, but more than four times as potent. 3-methyl-1-butanol and 2-ethyl-1-butanol each present a butanol moiety from two separate alignments. Dose response curves for inhibition of cell-cell adhesion were analyzed in L1-expressing NIH/3T3 cells. Maximal inhibition of cell-cell adhesion was comparable for all four alcohols (Table 1); however, potency differed several fold (FIG. 2), increasing as a function of the number of 1-butanol moieties rather than the molecular volume or the membrane/buffer partition coefficient.

EXAMPLE 5

The following example shows that long-chain alcohols antagonize the effects of short-chain alcohols on cell adhesion.

Although 1-alcohols longer than 1-butanol have no intrinsic activity, they might still antagonize the effects of shorter 1-alcohols by competing for binding at a putative hydrophobic target site. We used BMP-7 treated NG108-15 cells to test whether 1-pentanol or 1-octanol could antagonize the inhibition of cell-cell adhesion by a maximally effective concentration of 1-butanol (2 mM). Both 1-pentanol and 1-octanol completely abolished the effects of 1-butanol (FIG. 3).

Figure 3:
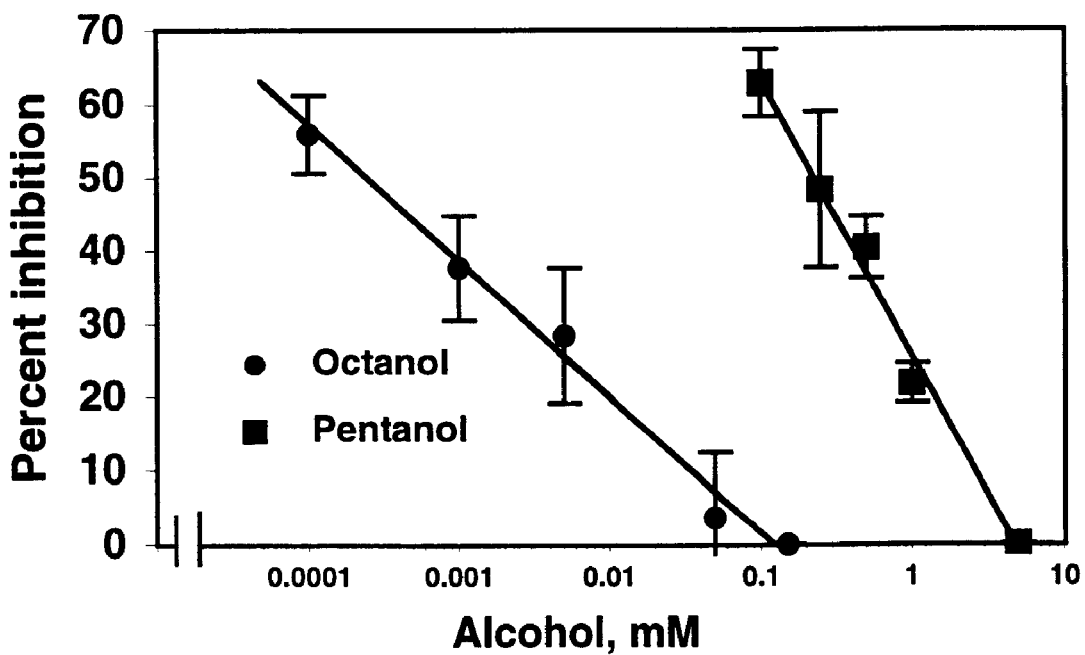
FIG. 3 is a graphical illustration of antagonism of 1-butanol inhibition of cell adhesion by 1-octanol and 1-pentanol.

FIG. 3 shows means for the percent inhibition of cell adhesion by 1-butanol (n=3–5). Cell adhesion assays were performed with BMP-7 treated NG108-15 cells in the presence of 2 mM 1-butanol and the indicated concentrations of 1-octanol or 1-pentanol. Similar results were obtained using L1-expressing NIH/3T3 cells expressing human L1. Antagonism was dosedependent, and 1-octanol ($IC_{50}$=3.6 $\mu$m) was approximately 200 times more potent than 1-pentanol ($IC_{50}$=715 $\mu$M). Both 1-pentanol and 1-octanol also abolished the effects of 100 mM ethanol and 3 mM 3-methyl-1-butanol. Similar results were obtained in L1 expressing NIH/3T3 cells (2B2-L1).

Figure 4:
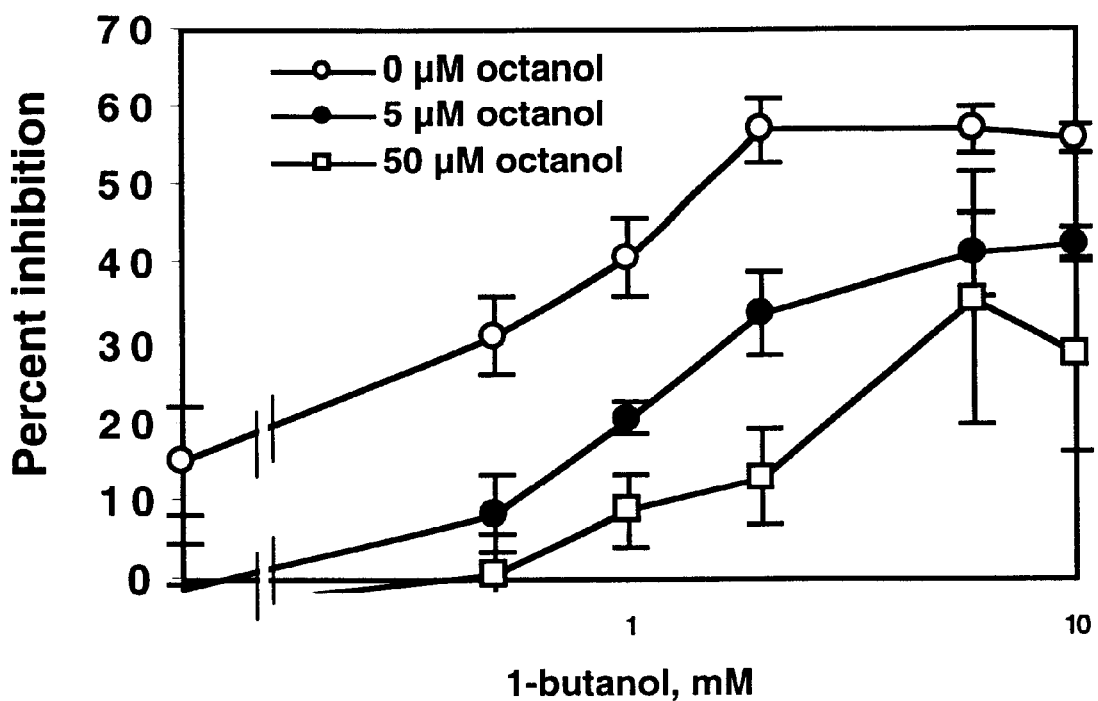
FIG. 4 shows dose response curves for 1-butanol inhibition of cell adhesion in NIH/3T3-L1 (2B2-L1) cells determined in the presence of the indicated concentrations of 1-octanol. Shown are the mean±SEM percent inhibition of cell adhesion for 3–5 experiments.

To explore the mechanism of antagonism, we performed dose response curves of 1-butanol in the absence and presence of two concentrations of 1-octanol (5 and 50 $\mu$M). 1-Octanol reduced the maximal effectiveness of 1-butanol in 2B2-L1 cells (FIG. 4), consistent with a non-competitive mechanism of inhibition. To determine whether 1-octanol was a reversible antagonist, 2B2L1 cells growing in T75 tissue culture flasks were incubated for 30 minutes at 37° C. in the absence and presence of 50 $\mu$M 1-octanol, washed 3 times with 10 ml of medium, and harvested for adhesion assays. Pretreatment with 1-octanol followed by washing did not reduce 1-butanol inhibition of cell-cell adhesion (1-butanol inhibition: control, 43.6±3.0%; 1-octanol pretreatment, 55.7±11%).

EXAMPLE 6

The following is an example showing that ethanol inhibition of BMP-7 morphogenesis is also antagonized by 1-octanol.

Treatment with BMP-7 for 48 hours causes NG108-15 cells to grow in clusters of adherent cells (BMP-7 morphogenesis), rather than as predominantly single cells. We showed previously that low concentrations of ethanol inhibit BMP-7 morphogenesis (Reference 10). We therefore determined whether 1-octanol could antagonize ethanol inhibition of BMP-7 morphogenesis. NG108-15 cells were cultured for 3 days in a serum-free medium supplemented with the indicated concentrations of BMP-7, ethanol, and 1-octanol (FIG. 6).

Figure 5A:
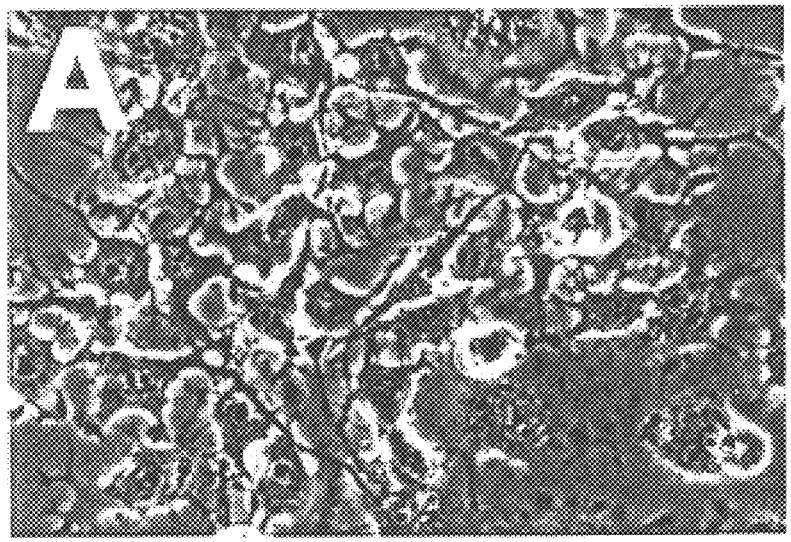
FIGS. 5A–5D are photomicrographs showing that ethanol inhibition of BMP-7 morphogenesis is also antagonized by 1-octanol.
Figure 5B:
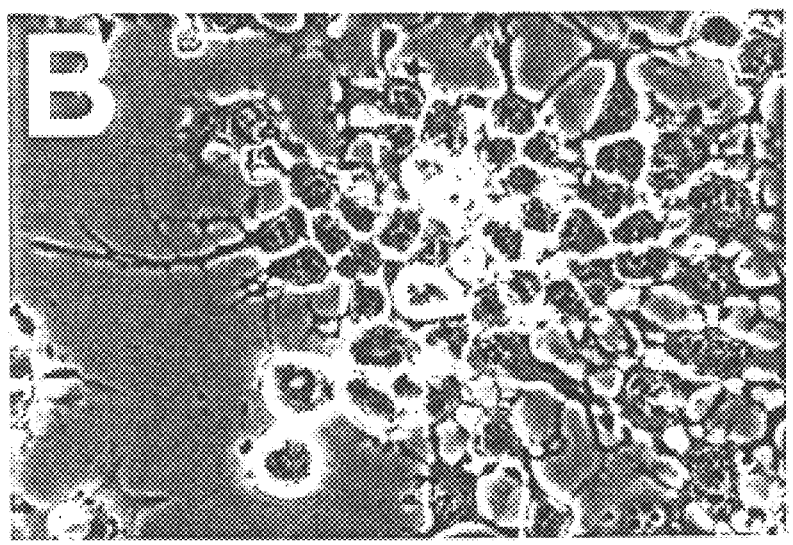
Figure 5C:
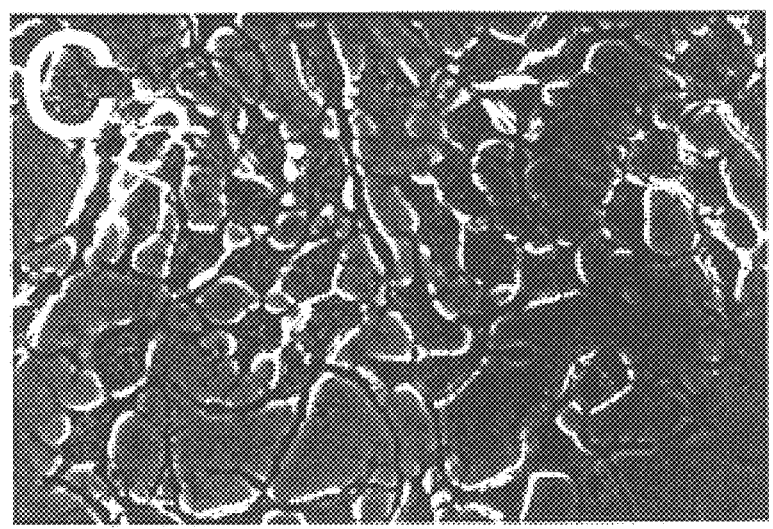
Figure 5D:
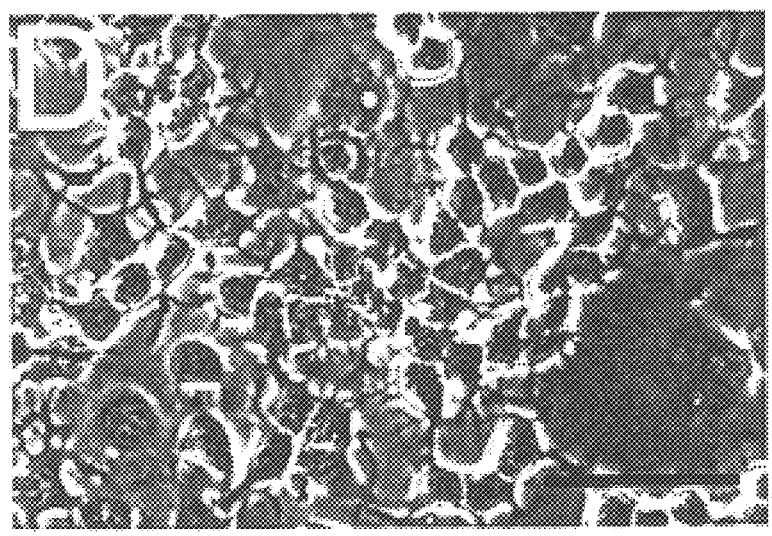

FIGS. 5A–5D are photomicrographs obtained under phase contrast microscopy (200×magnification) from the cells treated as follows: FIG. 5A—no additions (control); FIG. 5B—10 ng/ml BMP-7 ; FIG. 5C—10 ng/ml BMP-7 and 50 mM ethanol; and FIG. 5D—10 ng/ml BMP-7, 50 mM ethanol, and 0.05 mM 1-octanol.

Figure 6:
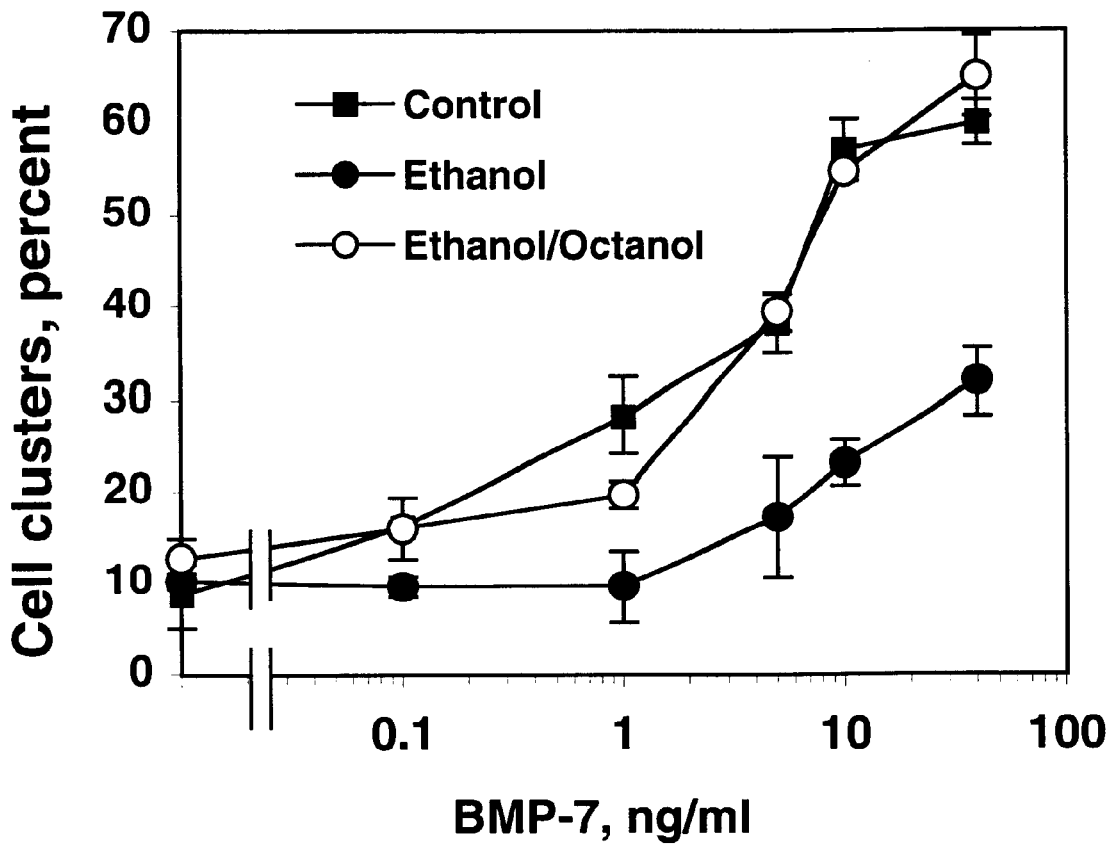
FIG. 6 shows the mean±SEM curves for the percentage of cell clusters.

FIG. 6 shows the mean±SEM for the percentage of cell clusters from 3–4 independent experiments (Scale bar=100 $\mu$m.) NG108-15 cells were cultured for 3 days in the presence of 0.1–40 ng/ml BMP-7. Parallel BMP-7-treated cultures were treated with 50 mM ethanol, or 50 mM ethanol and 0.05 mM 1-octanol. The percentage of cells in clusters of three or more cells was scored from two separate fields viewed under 200×magnification. BMP-7 caused a dose-dependent increase in the percentage of cell clusters, and this effect was inhibited significantly by 50 mM ethanol (FIG. 6). Octanol completely abolished ethanol inhibition of BMP-7 morphogenesis.

The above examples provide evidence for a highly specific interaction between alcohols and a target that regulates cell-cell adhesion. Alcohols of specific size and shape selectively inhibit cell-cell adhesion in L1-transfected NIH/3T3 cells and in BMP-7-treated NG108-15 cells. The pharmacological profile of twenty different alcohols is identical in the two cellular systems, consistent with the existence of a common molecular target. Previous data suggest that this target is L1 or an L1-associated protein (References 11–13).

Our structure activity analysis indicates that the alcohol target discriminates among alcohols of equivalent molecular volume and is exquisitely sensitive to molecular shape. Cell-cell adhesion is inhibited with increasing potency by methanol, ethanol, 1-propanol, and 1-butanol (References 10 and 11). This shows that short chain 1-alcohols interact with a hydrophobic recognition site. The existence of a cutoff above 1-butanol and cyclobutanol indicates that this site has limited dimensions. Membrane lipid solubility is not a critical determinant of alcohol action, because membrane/buffer partition coefficient increases sharply as a function of carbon chain length for alcohols across the range of active and inactive 1-alcohols (Reference 15). The total number of carbons is also not believed to be a critical determinant of activity. The most potent 1-butanol derivatives, 2-ethyl-butanol and 3-dimethyl-1-butanol, have more carbons (six) and larger molecular volumes than the inactive alcohol, 1-pentanol.

1-butanol is the most potent 1-alcohol, and molecules related to 1-butanol were the most informative about the structural requirements for alcohol activity. The addition of methyl groups to the 2- and 3-carbon positions increases potency. In fact, molecules that comprise multiple 1-butanol moieties appear to act as multivalent ligands. Derivatives of 1-butanol become inactive if there is restricted rotation between the third and fourth carbons (3-buten-1-ol and cyclopropylethanol) or interference with the hydroxyl group (2-pentanol). These data indicate that the target site is optimally engaged by molecules related to 1-butanol, but also imposes structural constraints on the presentation of the 1-butanol molecule. In this respect, alcohols appear to act like classical receptor ligands in inhibiting cell-cell adhesion.

Dwyer and Bradley have derived a loose consensus sequence features in alcohol sensitive proteins (Reference 8). In their model, the methyl groups of the alcohol lie within a hydrophobic cavity or groove, while the hydroxyl group participates as hydrogen bond donor. The hydrophobic groove and the hydrogen acceptor site are formed from several structural elements, such as loops and turns, often near an alpha-helix.

Our structure activity analysis is consistent with the presence of both a discrete hydrophobic binding groove and a nearby hydrophilic allosteric regulatory site. For 1-butanol, alignment of the hydroxyl group with the allosteric site must require some flexibility within the hydrophobic groove, because restriction of rotation about the 4-carbon abolishes activity. Alcohols longer than 1-butanol are believed to be inactive because they are too large to fit within the hydrophobic groove. Alternatively, long-chain 1-alcohols may fit within the hydrophobic groove, but project their hydroxyl groups too far from the allosteric site.

The presence of a highly selective target site predicts the existence of antagonists. A major discovery of this invention is that 1-pentanol and 1-octanol, though inactive alone, completely abolish the effects of 1-butanol or ethanol on cell-cell adhesion. 1-Octanol was found to be more potent than 1-pentanol, suggesting that antagonism also requires interaction with a hydrophobic site. This is believed to be the first demonstration that 1-alcohols above a cutoff can antagonize the actions of 1-alcohols below the cutoff. These data also provide the first description of a specific, non-enzymatic antagonist of ethanol in neural cells. Although the mechanism of antagonism remains unclear, we believe that the antagonists may compete with active alcohols for access to the hydrophobic target site. Alternatively, binding of the antagonists, may induce a conformational change that moves an allosteric site out of range of the active alcohols, without disrupting cell-cell adhesion. The non-competitive nature of antagonism by 1-octanol is more consistent with this latter possibility. Antagonism by long-chain alcohols is not a universal property of alcohol targets that exhibit a cutoff. 1-Octanol did not antagonize ethanol enhancement of GIRK ¼ potassium channel activity (Reference 20), which exhibits a cutoff effect between 1-propanol and 1-butanol.

To learn whether 1-octanol antagonism modifies the effects of ethanol on a cellular response that depends on cell adhesion, we used a cellular model in which the induction of L1 and N-CAM alters the morphology of proliferating neural cells. We showed previously that ethanol inhibits the morphological changes induced by BMP-7 in NG108-15 cells (Reference 10). Here we discovered that 1-octanol potently antagonizes inhibition of BMP-7 morphogenesis. Thus, 1-octanol antagonizes both the short term effects of ethanol on cell-cell adhesion and the long-term effects of ethanol in a morphogenetic assay of proliferating neural cells.

Among different clonal, L1-transfected NIH/3T3 cell lines, only a subset were ethanol-sensitive, suggesting that host-cell factors modify the effects of ethanol on L1-mediated cell-cell adhesion (Reference 12). Myeloma cells and insect SF9 cells transfected with L1 were insensitive to ethanol (References 14 and 21). In effect, 1-octanol converts L1-expressing NIH/3T3 cells from an ethanol-sensitive to an ethanol-insensitive phenotype. If long-chain alcohols can prevent ethanol interaction with L1, then other cell-specific, post-translational modifications of the molecule might do likewise.

As noted above, L1 plays a critical role in neural development (Reference 22) and has also been implicated in processes related to learning and memory (Reference 23). We believe that effects of ethanol on L1 and cell adhesion could contribute to the development of fetal alcohol syndrome and to cognitive impairment of alcoholics (Reference 11). Therefore, 1-octanol and related compounds may prove useful in dissecting the role of L1 and cell adhesion in both of these adverse effects of ethanol on the nervous system. L1 would be a candidate target for actions of ethanol that are blocked by low concentration of 1-octanol. Compounds that block ethanol effects on L1 might also reduce ethanol teratogenesis.

TABLE 1

Inhibition of cell-cell adhesion, membrane/buffer partition coefficient, and molar volume for a series of alcohols and non-volatile anesthetic.

| Alcohols | Concentration mM | Inhibition of Cell Cell Adhesion | | $P_{(m/b)}$ | $V_m$ (ml/mole) |
|---|---|---|---|---|---|
| | | NG108-15 | NIH/3T3-L1 | | |
| | | % ± SEM | | | |
| ethanol | 100 | 61 ± 3 | 58 ± 5 | 1.10 | 58 |
| cyclopropyl methanol | 13.5 | 55 ± 5 | 64 ± 10 | 0.71 | 71 |
| cyclopropyl-ethanol | 11.6 | 0 ± 1 | 4 ± 1 | 0.83 | 91 |
| cyclobutanol | 10.5 | 44 ± 12 | 46 ± 6 | 0.91 | 78 |
| 3-buten-1-ol | 9.6 | 3 ± 3 | 2 ± 6 | 1.00 | 86 |
| 2-methyl-1-propanol | 8.7 | 41 ± 7 | 51 ± 1 | 1.10 | 90 |
| 1-butanol | 2 | 52 ± 4 | 40 ± 4 | 1.52 | 92 |
| 2-methyl-2-butanol | 6.2 | 47 ± 8 | 47 ± 4 | 1.55 | 109 |
| cyclopentanol | 4.3 | 2 ± 1 | 0 ± 7 | 2.24 | 92 |
| benzyl alcohol | 3.8 | 0 ± 4 | 4 ± 4 | 2.52 | 104 |
| 3-methyl-1-butanol | 3.3 | 57 ± 6 | 51 ± 5 | 2.89 | 109 |
| 2-pentanol | 2.2 | 5 ± 6 | 11 ± 6 | 4.38 | 109 |
| 3-pentanol | 2.1 | 5 ± 9 | 10 ± 4 | 4.69 | 107 |
| 1-pentanol | 5 | 0 ± 3 | 7 ± 5 | 5.02 | 108 |
| 2-methyl-2-pentanol | 1.8 | 0 ± 2 | 2 ± 7 | 5.20 | 122 |
| 3,3-dimethyl-1-butanol | 1.7 | 42 ± 4 | 64 ± 20 | 5.77 | 121 |
| 2-ethyl-1-butanol | 1.1 | 43 ± 3 | 63 ± 12 | 9.14 | 123 |
| 4-methyl-1-pentanol | 1.1 | 7 ± 10 | 5 ± 3 | 9.36 | 126 |
| 1-octanol | 0.05 | 5 ± 4 | 3 ± 6 | 189 | 158 |
| propofol | 0.002 | 2 ± 6 | 5 ± 6 | 1.00 | 86 |

A pharmaceutical composition including 1-butanol, 1-octanol, or a structurally-related derivative thereof, may be prepared, in a conventional manner. In particular, a pharmaceutical composition made in accordance with the present invention would include 1-butanol, 1-octanol, or a structural derivative thereof in an amount sufficient to provide therapeutic and/or prophylactic benefit, in combination with one or more pharmaceutically or physiologically acceptable carriers, diluents or excipients. Compositions of the present invention may be formulated for any appropriate manner for administration, including, for example, oral, nasal, intravenous or intramuscular administration. Appropriate dosages, duration and frequency of administration would be determined by known factors, such as the condition of the patient, the type and severity of the disease and the method of administration.

While this invention has been described as having preferred ranges, steps, materials, or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the appended claims.

What is claimed is:

1. A method of antagonizing alcohol inhibition effects on cell adhesion, comprising:

contacting a cell-adhesion molecule expressing cell with an effective amount of a compound; and wherein the compound comprises an alcohol with five or more carbons.

2. The method of claim 1, wherein:

said cell-adhesion molecule comprises L1 molecule.

3. The method of claim 1, wherein:

said alcohol comprises a long-chain alcohol.

4. The method of claim 1, wherein:

said compound is selected from the group consisting of 1-pentanol, 1-octanol, and a derivative thereof.

5. The method of claim 1, wherein:

said cell-adhesion molecule expressing cell comprises a neural or fibroblast cell.

6. A method for the prophylaxis or treatment of toxic effects of alcohol, comprising:

administering to a subject in need thereof a pharmaceutical composition including an effective amount of an alcohol with five or more carbons.

7. The method of claim 6, wherein:

said alcohol is selected from the group consisting of 1-pentanol, 1-octanol, and a derivative thereof.

8. A method for the prophylaxis or treatment of fetal alcohol syndrome, memory disorder, malformations of the brain, cognitive learning disorders, addiction, neurobehavioral disorders, neurological disorders, or teratogenesis, comprising:

administering to a subject in need thereof a pharmaceutical composition including an effective amount of an alcohol with five or more carbons.

9. The method of claim 8, wherein:

said alcohol is selected from the group consisting of 1-pentanol, 1-octanol, and a derivative thereof.

* * * * *

UNITED STATES PATENT AND TRADEMARK OFFICE
CERTIFICATE OF CORRECTION

PATENT NO. : 6,359,015 B1 Page 1 of 1
APPLICATION NO. : 09/793533
DATED : March 19, 2002
INVENTOR(S) : Michael E. Charness and Michael F. Wilkemeyer It is certified that error appears in the above-identified patent and that said Letters Patent is hereby corrected as shown below:

Please insert the following paragraph at Column 1, after line 8:

--STATEMENT REGARDING FEDERALLY SPONSORED RESEARCH OR DEVELOPMENT

This invention was supported by grants AA011297 and AA009669 awarded by the National Institute of Health. The government has certain rights to this invention.--

Signed and Sealed this

Third Day of March, 2009

JOHN DOLL
*Acting Director of the United States Patent and Trademark Office*